(12) United States Patent
Paternuosto

(10) Patent No.: US 7,118,586 B1
(45) Date of Patent: Oct. 10, 2006

(54) FORCEPS FOR MEDICAL USE

(75) Inventor: Mario I. Paternuosto, Angelo In Formis (IT)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/111,372

(22) PCT Filed: Oct. 24, 2000

(86) PCT No.: PCT/IB00/01532

§ 371 (c)(1),
(2), (4) Date: Sep. 10, 2002

(87) PCT Pub. No.: WO01/30242

PCT Pub. Date: May 3, 2001

(30) Foreign Application Priority Data

Oct. 25, 1999 (IT) ............................... CE99A0004

(51) Int. Cl.
*A61B 17/28* (2006.01)
(52) U.S. Cl. ....................... 606/205; 600/570
(58) Field of Classification Search ................. 606/170, 606/167, 175, 185, 205, 207, 106, 110; 600/562, 600/564, 570, 582; 206/363, 403, 407, 414, 206/43 R See application file for complete search history.

(56) References Cited

U.S. PATENT DOCUMENTS

| | | | |
|---|---|---|---|
| 1,609,014 A | * | 11/1926 | Dowd ..................... 606/114 |
| 2,778,357 A | | 1/1957 | Leibinger et al. |
| 3,889,657 A | | 6/1975 | Baumgarten |
| 4,632,110 A | | 12/1986 | Sanagi |
| 4,646,751 A | * | 3/1987 | Maslanka ................ 600/564 |
| 4,669,471 A | | 6/1987 | Hayashi |
| 4,676,249 A | | 6/1987 | Arenas et al. |
| 4,712,545 A | | 12/1987 | Honkanen |
| 4,721,116 A | | 1/1988 | Schintgen et al. |
| 4,763,668 A | | 8/1988 | Macek et al. |
| 4,785,825 A | | 11/1988 | Romaniuk et al. |
| 4,815,460 A | | 3/1989 | Porat et al. |
| 4,815,476 A | | 3/1989 | Clossick |
| 4,817,630 A | | 4/1989 | Schintgen et al. |
| 4,880,015 A | | 11/1989 | Nierman |
| 4,887,612 A | | 12/1989 | Esser et al. |
| 4,889,118 A | | 12/1989 | Schwiegerling |
| 4,936,312 A | | 6/1990 | Tsukagoshi |
| 4,950,273 A | | 8/1990 | Briggs |
| 4,953,559 A | | 9/1990 | Salerno |
| 4,986,279 A | | 1/1991 | O'Neil |
| 5,037,379 A | | 8/1991 | Clayman et al. |
| 5,052,402 A | | 10/1991 | Bencini et al. |
| 5,059,214 A | | 10/1991 | Akopov et al. |

(Continued)

FOREIGN PATENT DOCUMENTS

DE      8712328 U1      3/1988

(Continued)

*Primary Examiner*—Julian W. Woo
*Assistant Examiner*—Victor Nguyen
(74) *Attorney, Agent, or Firm*—Finnegan, Henderson, Farabow, Garrett & Dunner LLP

(57) ABSTRACT

Forceps having two-half shells are disclosed. Each half-shell includes a front rim and a base wall and is mounted on a support element in a manner such that the half-shells can adopt a first opened-out configuration and a second closed configuration. The forceps include at least one container element having a cavity for receiving a plurality of biopsy samples. The container element is preferably associated with one of the half-shells.

67 Claims, 4 Drawing Sheets

U.S. PATENT DOCUMENTS

| | | | |
|---|---|---|---|
| 5,074,867 A | 12/1991 | Wilk | |
| 5,082,000 A | 1/1992 | Picha et al. | |
| 5,147,371 A * | 9/1992 | Washington et al. | 606/127 |
| 5,152,778 A | 10/1992 | Bales, Jr. et al. | |
| 5,171,256 A | 12/1992 | Smith et al. | |
| 5,172,700 A * | 12/1992 | Bencini et al. | 600/564 |
| 5,190,542 A * | 3/1993 | Nakao et al. | 606/47 |
| 5,190,555 A | 3/1993 | Wetter et al. | |
| 5,192,284 A | 3/1993 | Pleatman | |
| 5,201,740 A | 4/1993 | Nakao et al. | |
| 5,241,968 A | 9/1993 | Slater | |
| 5,263,967 A | 11/1993 | Lyons, III et al. | |
| 5,330,502 A | 7/1994 | Hassler et al. | |
| 5,341,815 A | 8/1994 | Cofone et al. | |
| 5,342,389 A | 8/1994 | Haber et al. | |
| 5,348,023 A | 9/1994 | McLucas | |
| 5,366,467 A | 11/1994 | Lynch et al. | |
| 5,368,597 A | 11/1994 | Pagedas | |
| 5,374,227 A | 12/1994 | Webb | |
| 5,374,277 A | 12/1994 | Hassler | |
| 5,383,888 A | 1/1995 | Zvenyatsky et al. | |
| 5,423,854 A | 6/1995 | Martin et al. | |
| 5,535,754 A | 7/1996 | Doherty | |
| 5,538,008 A * | 7/1996 | Crowe | 600/564 |
| 5,542,432 A * | 8/1996 | Slater et al. | 600/564 |
| 5,558,100 A | 9/1996 | Cox | |
| 5,564,436 A | 10/1996 | Hakky et al. | |
| 5,569,299 A * | 10/1996 | Dill et al. | 606/205 |
| 5,571,129 A | 11/1996 | Porter | |
| 5,584,855 A * | 12/1996 | Onik | 606/207 |
| 5,643,283 A | 7/1997 | Younker | |
| 5,643,307 A * | 7/1997 | Turkel et al. | 606/184 |
| 5,662,671 A * | 9/1997 | Barbut et al. | 606/170 |
| 5,681,324 A | 10/1997 | Kammerer et al. | |
| 5,681,348 A | 10/1997 | Sato | |
| 5,683,413 A | 11/1997 | Miyagi | |
| 5,707,392 A | 1/1998 | Kortenbach | |
| 5,720,754 A | 2/1998 | Middleman et al. | |
| 5,746,740 A | 5/1998 | Nicholas | |
| 5,759,187 A | 6/1998 | Nakao et al. | |
| 5,762,070 A | 6/1998 | Nagamatsu | |
| 5,762,613 A | 6/1998 | Sutton et al. | |
| 5,779,646 A | 7/1998 | Koblish et al. | |
| 5,810,876 A | 9/1998 | Kelleher | |
| 5,820,630 A | 10/1998 | Lind | |
| 5,843,000 A | 12/1998 | Nishioka et al. | |
| 5,853,374 A | 12/1998 | Hart et al. | |
| 5,906,621 A | 5/1999 | Secrest et al. | |
| 5,908,437 A | 6/1999 | Asano et al. | |
| 5,919,206 A | 7/1999 | Gengler et al. | |
| 5,951,488 A * | 9/1999 | Slater et al. | 600/564 |
| 5,971,940 A | 10/1999 | Baker et al. | |
| 6,007,546 A | 12/1999 | Snow et al. | |
| 6,013,095 A | 1/2000 | Ouchi | |
| 6,019,770 A | 2/2000 | Christoudias | |
| RE36,666 E | 4/2000 | Honkanen et al. | |
| 6,071,248 A * | 6/2000 | Zimmon | 600/566 |
| 6,074,408 A | 6/2000 | Freeman | |
| 6,083,240 A | 7/2000 | Ouchi | |
| 6,106,553 A | 8/2000 | Feingold | |
| 6,129,683 A | 10/2000 | Sutton et al. | |
| 6,159,162 A | 12/2000 | Kostylev et al. | |
| 6,190,399 B1 | 2/2001 | Palmer et al. | |
| 6,228,095 B1 | 5/2001 | Dennis | |
| 6,273,860 B1 | 8/2001 | Kostylev et al. | |
| 6,299,630 B1 | 10/2001 | Yamamoto | |
| 6,309,404 B1 | 10/2001 | Krzyzanowski | |
| 6,368,290 B1 | 4/2002 | Baska | |
| 6,375,661 B1 | 4/2002 | Chu et al. | |
| 6,378,351 B1 | 4/2002 | Ouchi et al. | |
| 6,409,678 B1 | 6/2002 | Ouchi | |
| 6,409,733 B1 | 6/2002 | Conlon et al. | |
| 6,425,910 B1 | 7/2002 | Hugueny et al. | |
| 6,427,509 B1 | 8/2002 | Ouchi et al. | |
| 6,440,085 B1 | 8/2002 | Krzyzanowski | |
| 6,443,909 B1 | 9/2002 | Ouchi | |
| 6,514,197 B1 | 2/2003 | Ouchi et al. | |
| 6,514,269 B1 | 2/2003 | Yamamoto | |
| 6,554,850 B1 | 4/2003 | Ouchi et al. | |
| 6,607,227 B1 | 8/2003 | Morton | |
| 6,613,068 B1 | 9/2003 | Ouchi | |
| 6,673,092 B1 | 1/2004 | Bacher | |
| 6,685,723 B1 | 2/2004 | Ouchi et al. | |
| 6,689,122 B1 | 2/2004 | Yamamoto | |
| 6,695,791 B1 | 2/2004 | Gonzalez | |
| 6,709,445 B1 | 3/2004 | Boebel et al. | |
| 6,736,781 B1 | 5/2004 | Lee | |
| 6,740,106 B1 | 5/2004 | Kobayashi et al. | |
| 6,743,228 B1 | 6/2004 | Lee et al. | |
| 6,752,822 B1 | 6/2004 | Jespersen | |
| 6,792,663 B1 | 9/2004 | Krzyzanowski | |
| 6,805,699 B1 | 10/2004 | Shimm | |
| 6,808,491 B1 | 10/2004 | Kortenbach et al. | |
| 2001/0000348 A1 | 4/2001 | Chu et al. | |
| 2001/0047124 A1 | 11/2001 | Yamamoto | |
| 2002/0013595 A1 | 1/2002 | Yamamoto | |
| 2002/0156395 A1 | 10/2002 | Stephens et al. | |
| 2003/0040681 A1 | 2/2003 | Ng et al. | |
| 2003/0097147 A1 | 5/2003 | Prestel | |
| 2003/0105402 A1 | 6/2003 | Lee | |
| 2003/0163179 A1 | 8/2003 | Lee et al. | |
| 2003/0191464 A1 | 10/2003 | Kidooka | |
| 2003/0212342 A1 | 11/2003 | Rudnick et al. | |
| 2003/0229292 A1 | 12/2003 | Hibner et al. | |
| 2003/0229293 A1 | 12/2003 | Hibner et al. | |
| 2004/0015165 A1 | 1/2004 | Kidooka | |
| 2004/0024333 A1 | 2/2004 | Brown | |
| 2004/0034310 A1 | 2/2004 | McAlister et al. | |
| 2004/0059345 A1 | 3/2004 | Nakao et al. | |
| 2004/0068291 A1 | 4/2004 | Suzuki | |
| 2004/0087872 A1 | 5/2004 | Anderson et al. | |
| 2004/0087979 A1 | 5/2004 | Field et al. | |
| 2004/0092967 A1 | 5/2004 | Sancoff et al. | |
| 2004/0097829 A1 | 5/2004 | McRury et al. | |
| 2004/0138587 A1 | 7/2004 | Lyons | |
| 2004/0199159 A1 | 10/2004 | Lee et al. | |
| 2004/0220496 A1 | 11/2004 | Gonzalez | |
| 2004/0254592 A1 | 12/2004 | DiCarlo et al. | |

FOREIGN PATENT DOCUMENTS

| | | |
|---|---|---|
| DE | 8814560 U1 | 3/1989 |
| DE | 3920706 A1 | 1/1991 |
| DE | 4006673 A1 | 9/1991 |
| DE | 9211834 U1 | 4/1993 |
| DE | 68913909 T2 | 10/1994 |
| DE | 695 27 152 T2 | 6/1996 |
| DE | 29614931 U1 | 3/1997 |
| DE | 69310072 T2 | 11/1997 |
| DE | 69404526 T2 | 12/1997 |
| DE | 69319668 T2 | 12/1998 |
| DE | 10018674 A1 | 11/2000 |
| DE | 10048369 A1 | 4/2001 |
| DE | 10048369 C2 | 4/2001 |
| DE | 10051651 A1 | 4/2001 |
| DE | 10056946 A1 | 5/2001 |
| DE | 10128553 A1 | 1/2002 |
| DE | 10123848 A1 | 2/2002 |
| DE | 10156313 A1 | 6/2003 |
| DE | 10316134 A1 | 10/2003 |
| DE | 10332613 A1 | 2/2004 |
| EP | 0 207 829 A1 | 1/1987 |
| EP | 0 207 830 A1 | 1/1987 |
| EP | 0 279 358 A2 | 8/1988 |

| | | | | | | | |
|---|---|---|---|---|---|---|---|
| EP | 0 279 358 | B1 | 8/1988 | JP | 2001-137998 | A | 5/2001 |
| EP | 0 380 874 | A1 | 8/1990 | JP | 3190029 | B2 | 7/2001 |
| EP | 0 367 818 | B1 | 3/1994 | JP | 2001-517468 | A | 10/2001 |
| EP | 0 585 921 | A1 | 3/1994 | JP | 3220165 | B2 | 10/2001 |
| EP | 0 593 929 | A1 | 4/1994 | JP | 2001-321386 | A | 11/2001 |
| EP | 0 592 243 | B1 | 4/1997 | JP | 2002-011014 | A | 1/2002 |
| EP | 0 621 009 | B1 | 7/1997 | JP | 2002-065598 | A | 3/2002 |
| EP | 0 573 817 | B1 | 7/1998 | JP | 2003-093393 | A | 4/2003 |
| EP | 0 798 982 | B1 | 6/2002 | JP | 2004-000424 | A | 1/2004 |
| EP | 1 240 870 | A1 | 9/2002 | JP | 2004-049330 | A | 2/2004 |
| EP | 1 252 863 | A1 | 10/2002 | WO | WO 89/10093 | A1 | 11/1989 |
| EP | 1 312 313 | A1 | 5/2003 | WO | WO 90/01297 | A1 | 2/1990 |
| EP | 1 348 378 | A1 | 10/2003 | WO | WO 94 13215 | | 6/1994 |
| EP | 1 371 332 | A1 | 12/2003 | WO | WO 94/26172 | A1 | 11/1994 |
| EP | 1 001 706 | B1 | 3/2004 | WO | WO 94/26181 | A1 | 11/1994 |
| JP | S62-049838 | A | 3/1987 | WO | WO 95/20914 | A1 | 8/1995 |
| JP | H09-215747 | A | 8/1987 | WO | WO 96/19144 | A1 | 6/1996 |
| JP | S62-176438 | A | 8/1987 | WO | WO 96/24289 | A2 | 8/1996 |
| JP | H03-139340 | A | 6/1991 | WO | WO 97/41776 | A1 | 11/1997 |
| JP | H04-307050 | A | 10/1992 | WO | WO 97/41777 | A1 | 11/1997 |
| JP | H05-220157 | A | 8/1993 | WO | WO 98/06336 | A1 | 2/1998 |
| JP | H05-237120 | A | 9/1993 | WO | WO 98/35615 | A1 | 8/1998 |
| JP | H06-030942 | A | 2/1994 | WO | WO 99/07287 | A1 | 2/1999 |
| JP | H06-114063 | A | 4/1994 | WO | WO 99/15073 | A1 | 4/1999 |
| JP | H06-189966 | A | 7/1994 | WO | WO 99/20096 | A2 | 4/1999 |
| JP | H06-197906 | A | 7/1994 | WO | WO 99/53851 | A1 | 10/1999 |
| JP | H08-206120 | A | 8/1996 | WO | WO 00/01304 | A1 | 1/2000 |
| JP | H08-224242 | A | 9/1996 | WO | WO 00/07502 | A1 | 2/2000 |
| JP | H09-508561 | T2 | 9/1997 | WO | WO 00 33743 | | 6/2000 |
| JP | H09-276282 | A | 10/1997 | WO | WO 00/54658 | A1 | 9/2000 |
| JP | 10-099342 | | 4/1998 | WO | WO 01/30242 | A1 | 5/2001 |
| JP | H10-137246 | A | 5/1998 | WO | WO 02/062226 | A1 | 8/2002 |
| JP | H10-137250 | A | 5/1998 | WO | WO 02/062227 | A1 | 8/2002 |
| JP | H10-137251 | A | 5/1998 | WO | WO 03/022157 | A2 | 3/2003 |
| JP | H11-076244 | A | 3/1999 | WO | WO 03/024300 | A2 | 3/2003 |
| JP | 3220164 | B2 | 8/1999 | WO | WO 03/028557 | A1 | 4/2003 |
| JP | H11-509132 | T2 | 8/1999 | WO | WO 03/082119 | A1 | 10/2003 |
| JP | H11-509459 | T2 | 8/1999 | WO | WO 03/082122 | A1 | 10/2003 |
| JP | H11-239582 | A | 9/1999 | WO | WO 03/105674 | A2 | 12/2003 |
| JP | 2000-279418 | A | 10/2000 | WO | WO 2004/010874 | A1 | 2/2004 |
| JP | 2000-296131 | A | 10/2000 | | | | |
| JP | 2001-095808 | A | 4/2001 | | | | |
| JP | 2001-112763 | A1 | 4/2001 | | | | |

\* cited by examiner

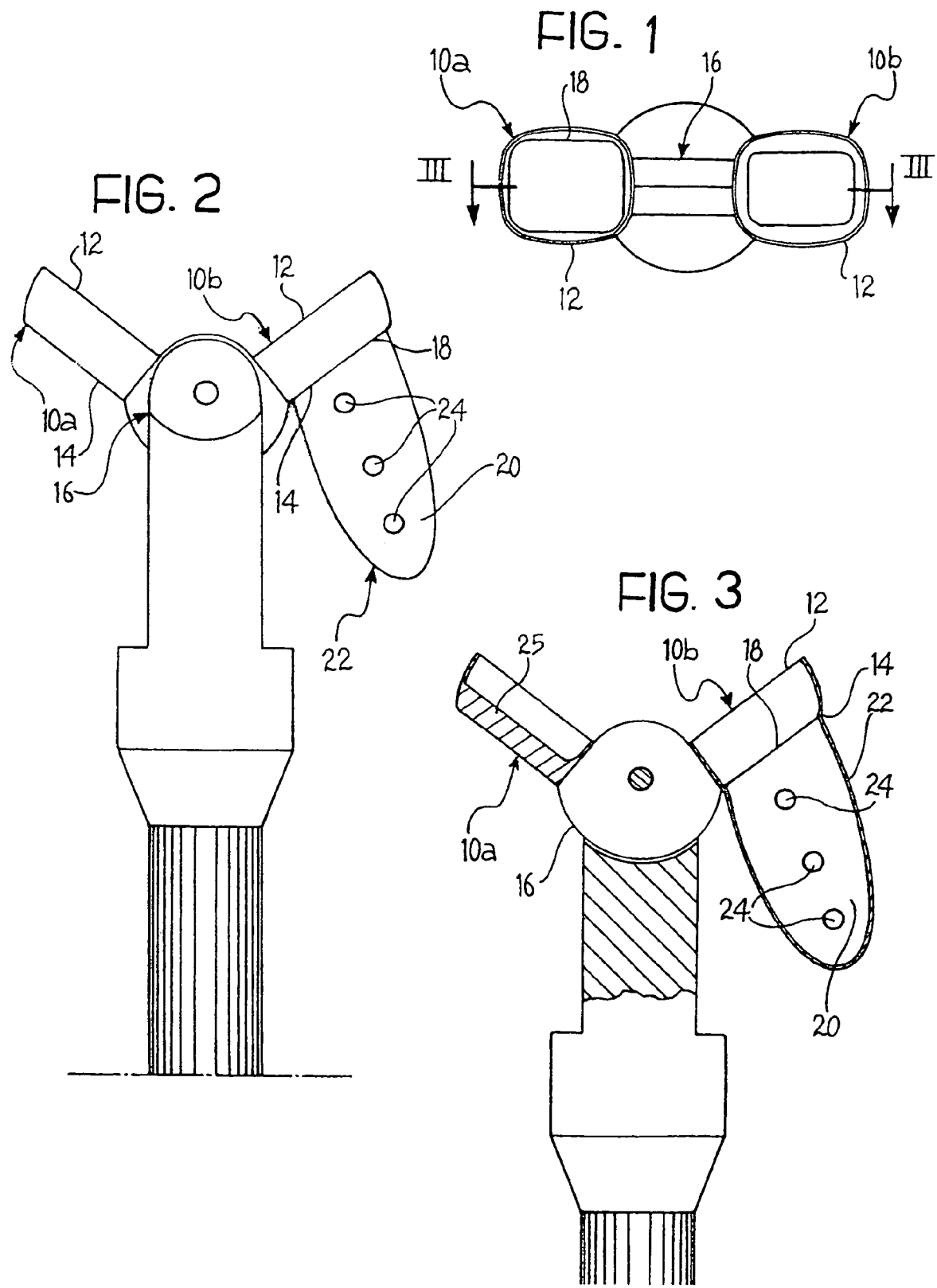

FORCEPS FOR MEDICAL USE

This application claims priority to International Application No. PCT/IB00/01532, filed Oct. 24, 2000, and Italian Application No. CE99A000004, filed Oct. 25, 1999.

The present invention relates to forceps for medical use, in particular for biopsy, for example, for endoscopic biopsy, laparoscopy, gynaeocological applications and the like.

More specifically, a conventional forceps of this type comprises two half-shells, each of which has a front rim and a base wall, and which are mounted on a support element in a manner such that they can adopt a first, opened-out configuration and a second, closed configuration.

In use, for example, during digestive endoscopy, the forceps is passed through the operating duct of an endoscope in the closed configuration and is brought into contact with the internal mucosa of the organ (for example, the oesophagus, stomach, duodenum, or colon) to be biopsied.

Once the forceps has been positioned correctly, the half-shells are opened and then closed so as to cut off a sample of the mucosa which remains held between them. Given the intrinsically limited nature of the space available, the closed half-shells can hold at most 2–3 biopsy samples.

However, pathological conditions frequently occur in which the number of samples taken has to be greater, as with gastric ulcers, or dysplasia or neoplasia in ulcerative pancolitis, which is a serious chronic disease of the colon.

In these cases, each time the space inside the half-shells is filled with biopsy samples, the forceps has to be withdrawn through the endoscope duct, emptied and reintroduced to the operation site. A large amount of wear and deformation of the duct thus takes place, with the risk of rupture and consequent infiltration of liquid which may cause very serious damage to the endoscope.

Another problem connected with the need to perform a plurality of introductions and withdrawals of the forceps consists of the long duration of this procedure which is due, among other things, to the need to empty the half-shells. Owing to the small size of the samples taken, this operation in fact takes the operator a considerable amount of time. In operative practice, however, the time available—in certain conditions, for example, with markedly intolerant patients who are unable to take sedatives—may be limited, so that the use of conventional forceps is difficult.

To prevent the problems of the prior art mentioned above, the subject of the present invention is forceps of the type described at the beginning of the present description and characterized in that it has at least one container element having a cavity for receiving a plurality of biopsy samples.

The forceps of the invention can therefore be used to take all of samples necessary for a given pathological condition, in succession, by performing only one introduction and withdrawal, thus considerably reducing the time required for the operation, as well as the wear of the endoscope duct.

Moreover, during the withdrawal stage, the container element keeps the biopsy samples isolated from the duct, which has the advantage of preventing any mixing with impurities or with any scraps remaining from other samples taken, which may be present therein.

Further advantages and characteristics of the present description, provided by way of non-limiting example with reference to the appended drawings, in which:

FIG. 1 is a schematic plan view of a forceps of the invention,

FIG. 2 is a front elevational view of the forceps of FIG. 1,

FIG. 3 is a section view taken on the line III—III of FIG. 1,

Figure 4:
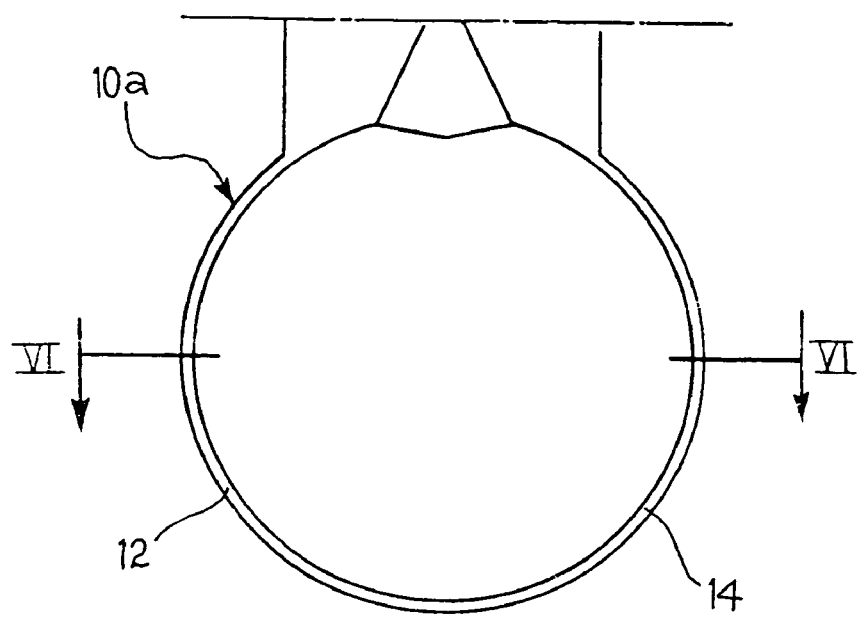
Figure 5:
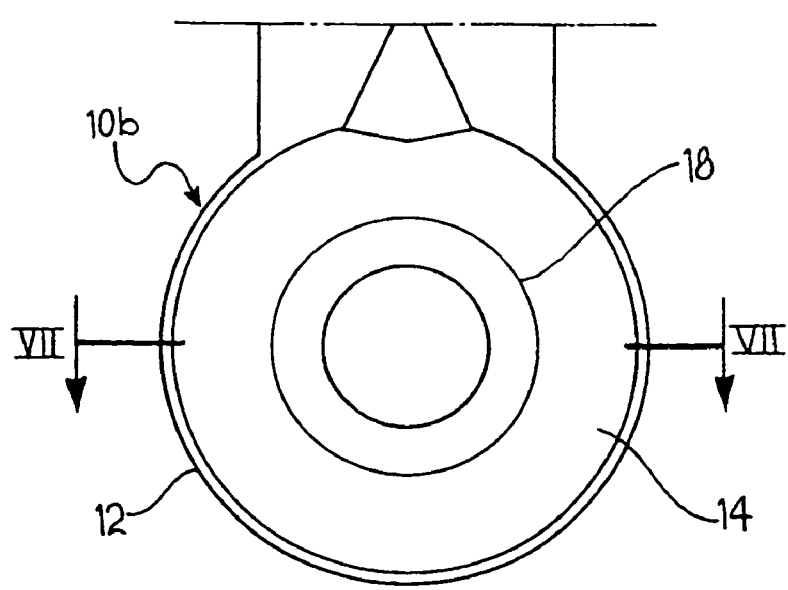
Figure 6:
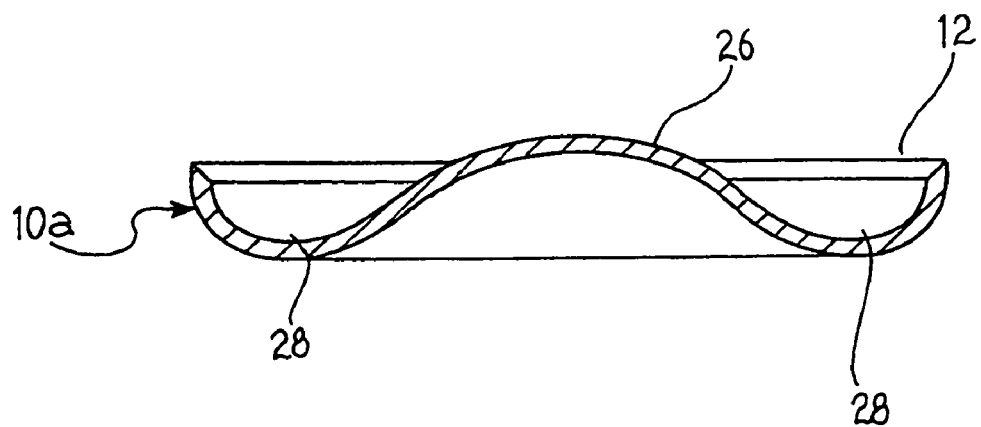
Figure 7:
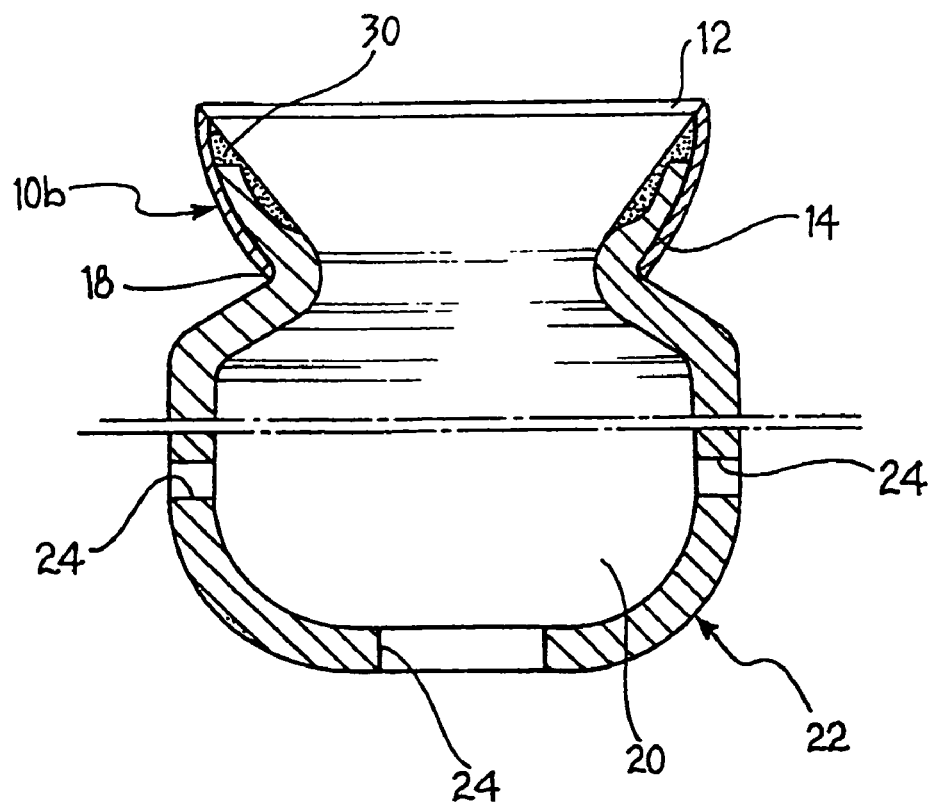
Figure 8:
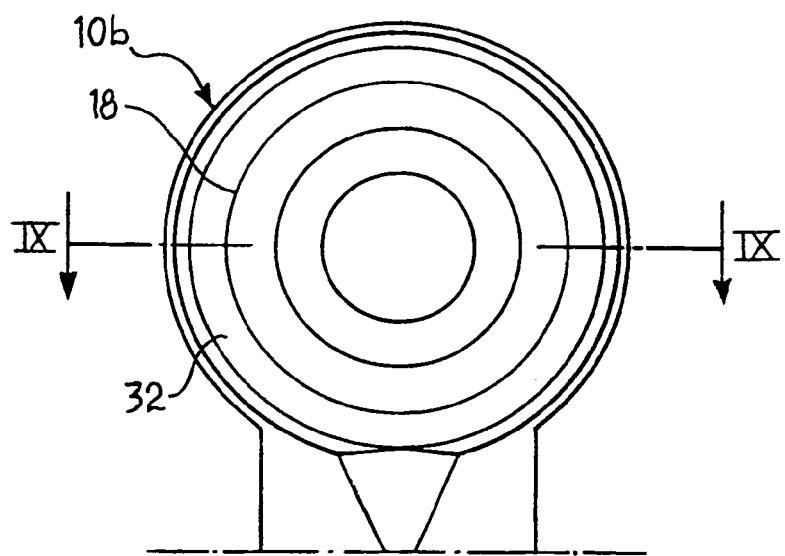
Figure 9:
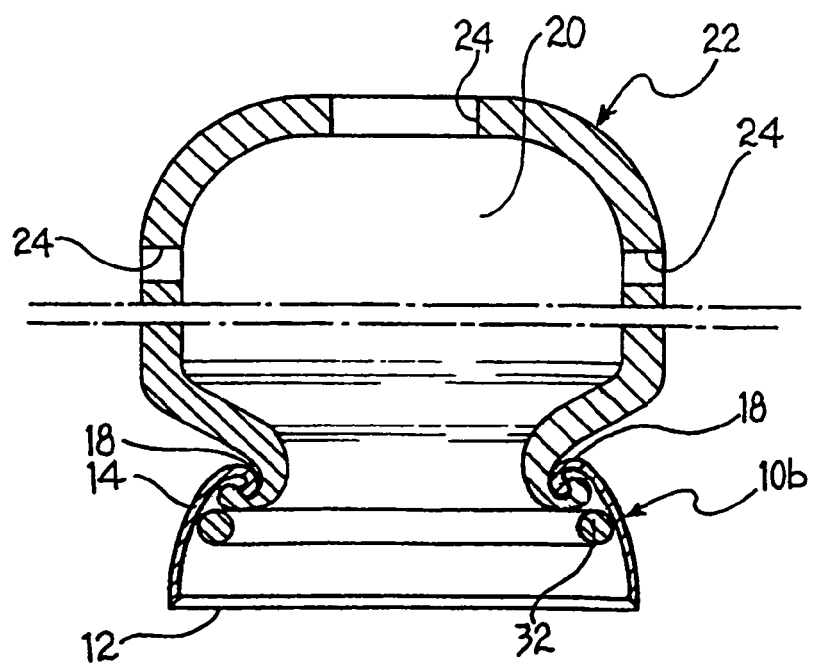

FIGS. 4 and 5 are respective plan views of each of the two half-shells of a forceps constituting an alternative embodiment of the invention, FIG. 6 is a section taken on the line VI—VI of FIG. 4, FIG. 7 is a section view taken on the line VII—VII of FIG. 5, and FIGS. 8 and 9 are views corresponding to FIGS. 5 and 7, respectively, of a further embodiment of a detail of a forceps of the invention.

A biopsy forceps, for example, for endoscopic biopsy, comprises (FIGS. 1–3) two half-shells 10a, 10b each having a front rim 12 and a base wall 14. The half-shells 10a, 10b are mounted in conventional manner, for example, on a support element 16 so that they can adopt a first, opened-out configuration (shown in the drawings) and a second, closed configuration in which the rims 12 of the two half-shells 10a, 10b are in contact with one another.

The half-shell 10b has, in its base wall 14, a hole 18 which communicates with the cavity 20 inside a beaker-shaped container element 22 associated therewith and having a plurality of through-openings 24 in its walls.

The material constituting the element 22 is not critical within the scope of the present invention and may be selected, without particular limitations, from those suitable for use in the medical field.

The half-shell 10a, on the other hand, is filled up to approximately a third of its height with filling material 25.

In use, the forceps is first of all passed through an endoscope duct (not shown in the drawings), with the half-shells 10a, 10b in the closed configuration, until the forceps is in the desired location close to the internal mucosa of the organ to be biopsied. Here, the half-shells 10a, 10b are opened out and closed again several times in succession so as to cut off a corresponding number of biopsy samples.

As these samples are taken one by one, they are urged towards the base of the container element 22 by the pressure exerted by the half-shell 10a.

The openings 24 allow air and any organic liquids which remain trapped in the cavity 20 of the element 22 to be discharged, further facilitating the movement of the biopsy samples inside the element 22.

Upon completion of the cutting of the samples, the half-shells 10a, 10b are closed again and the forceps, with its duct. The biopsy samples which are enclosed inside the cavity 20 do not therefore have any substantial contact with the duct, which could constitute a potential source of histological contamination.

FIGS. 4 to 7 show an alternative embodiment of the half-shells of a biopsy forceps according to the invention, which half-shells can be mounted on a support element in a manner similar to that described with reference to FIGS. 1–3.

In this embodiment, the half-shell 10a with which the container element 20 is not associated has (FIGS. 4 and 6) a base wall 14 having a central portion 26 which is raised substantially to the level of the rim 12, and an annular, recessed, peripheral portion 28.

The half-shell 10b, on the other hand, (FIGS. 5 and 7) has, in its base wall 14, the hole 18 in which the end of the beaker-shaped container element 22 is fixed by means of an annular layer of adhesive 30, this end being open and having a restricted neck. The internal cavity 20 of the container element 22 thus constitutes a continuation of the space inside the half-shell 10b.

The container element 22 also has openings 24 in its base and side walls.

The principle of the operation of the forceps having the half-shells just mentioned is substantially similar to that described with reference to FIGS. 1–3. The particular shape of the half-shell 10a enables a greater pressure to be exerted on the biopsy samples, directing them towards the cavity 20 of the element 22.

FIGS. 8 and 9 show a variant of the fixing of the container element 22 to the half-shell 10b, which is an alternative to the use of the above-described layer of adhesive. In this case, the open end of the element 22 has a hooked rim for engaging a rim of complementary shape of the hole 18 of the half-shell 10b. This engagement is preferably secured by a mechanical element such as a spring ring 32.

Naturally, the principle of the invention remaining the same, the details of construction and forms of embodiment may be varied widely with respect to those described purely by way of example, without thereby departing from its scope. In particular, both of the half-shells may have their own container elements and/or may have, independently of one another, any shape, for example, with a toothed or serrated rim. The container element in turn may have substantially any shape and/or length and/or may be in the form of a net engaged directly on the rim of the associated half-shell. Moreover, the container element may equally well be secured on the respective half-shell immovably, or releasably.

The invention claimed is:

1. Forceps for medical use, in particular for biopsy, comprising:
   a first and a second half-shell, each having a front rim and a base wall, the first and the second half-shells each being mounted on a support element in a manner such that the first and the second half-shells can adopt a first, open configuration and a second, closed configuration; and
   a container element associated with at least the first half-shell, the container element having a cavity for receiving a plurality of biopsy samples, wherein the container element is received in a hole defined by the base wall of the first half-shell,
   wherein the base wall of the second half-shell includes a central portion raised toward the front rim of the second half-shell.

2. Forceps according to claim 1, wherein the central portion is raised substantially to the level of the rim, and the base wall of the second half-shell further includes an annular, recessed, peripheral portion.

3. Forceps according to any one of the preceding claims, wherein the hole communicates with the cavity of the container element associated with the first half-shell.

4. Forceps according to claim 3, wherein the container element is beaker-shaped and is fixed in the hole such that the cavity constitutes a continuation of a space inside the first half-shell.

5. Forceps according to claim 4, wherein the container element includes an open end fixed to the first half-shell by an annular layer of adhesive.

6. Forceps according to claim 4, wherein the container element includes an open end having a hooked rim for engaging the front rim of the first half-shell.

7. Forceps according to claim 6, wherein the engagement of the hooked rim of the open end of the container element with the front rim of the hole of the first half-shell is secured by a mechanical element.

8. Forceps according to claim 7, wherein the mechanical element is a spring ring.

9. Forceps according to claim 6, wherein the front rim of the first half-shell is a complementary shape of the hooked rim of the container element.

10. Forceps according to claim 3, wherein the container element is beaker-shaped and includes a container base and side walls, and has at least one opening in the container base or in the side walls.

11. Forceps according to claim 1, wherein the container element is beaker-shaped and includes a container base and side walls, and has at least one opening in the container base or in the side walls.

12. Forceps according to claim 11, wherein the container element has a plurality of openings in the container base and in the side walls.

13. Forceps according to claim 1, wherein at least a portion of the container element is completely encircled by the base wall.

14. Forceps according to claim 1, wherein the hole is configured to pass the plurality of biopsy samples therethrough.

15. A biopsy forceps, comprising:
    a support element;
    a first half-shell supported by the support element, the first half-shell having a first front rim and a base wall;
    a second half-shell supported by the support element, the second half-shell having a second front rim, the first and the second half-shells being operatively configured to open and close to take biopsy samples; and
    a container element affixed to the first half-shell, the container element having a first opening to a cavity for receiving the biopsy samples, and a second opening for discharging fluid from the cavity, wherein the container element is received in a hole defined by the base wall of the first half-shell,
    wherein a base wall of the second half-shell includes a central portion raised toward the front rim of the second half-shell.

16. A biopsy forceps according to claim 15, wherein the central portion is raised substantially to the level of the rim, and the base wall of the second half-shell further includes an annular, recessed, peripheral portion.

17. A biopsy forceps according to claim 15, wherein the first half-shell includes a hole which communicates with the first opening to the cavity of the container element affixed to the first half-shell.

18. A biopsy forceps according to claim 17, wherein the container element is beaker-shaped and the cavity is in communication with a space inside the first half shell.

19. Forceps according to claim 15, wherein at least a portion of the container element is completely encircled by the base wall.

20. Forceps according to claim 15, wherein the hole is configured to pass the biopsy samples therethrough.

21. Forceps for medical use, in particular for biopsy, comprising:
a first and a second half-shell, each having a front rim and a base wall, the first and the second half-shells each being mounted on a support element in a manner such that the first and the second half-shells can adopt a first, open configuration and a second, closed configuration, the first and second half-shells being configured so that the front rims come into contact with each other when in the closed configuration; and
a container element associated with at least the first half-shell, the container element having a cavity for receiving a plurality of biopsy samples,
wherein the base wall of the second half-shell includes a central portion raised toward the front rim of the second half-shell,
wherein the base wall of the first half-shell includes a hole in which the container element is received.

22. Forceps according to claim 21, wherein the container element is beaker-shaped and includes a container base and side walls, and has at least one opening in the container base or in the side walls.

23. Forceps according to claim 21, wherein the hole communicates with the cavity of the container element associated with the first half-shell.

24. Forceps according to claim 21, wherein the container element is fixed in the hole such that the cavity constitutes a continuation of a space inside the first half-shell.

25. Forceps according to claim 21, wherein the central portion is raised substantially to the level of the rim, and the base wall of the second half-shell further includes an annular, recessed, peripheral portion.

26. Forceps according to claim 21, wherein the container element has a plurality of openings in the container base and in the side walls.

27. Forceps according to claim 21, wherein at least a portion of the container element is completely encircled by the base wall.

28. Forceps according to claim 21, wherein the hole is configured to pass the plurality of biopsy samples therethrough.

29. Forceps for medical use, in particular for biopsy, comprising:
a first and a second half-shell, each having a front rim and a base wall, the first and the second half-shells each being mounted on a support element in a manner such that the first and the second half-shells can adopt a first, open configuration and a second, closed configuration, wherein the first half-shell includes a hole in the base wall configured to pass a biopsy sample; and
a container element associated with the first half-shell, the container element having an open end for receiving the biopsy sample into a cavity sized to contain a plurality of biopsy samples, the open end corresponding in size to the hole in the base wall of the first half-shell,
wherein the base wall of the second half-shell includes a central portion raised toward the front rim of the second half-shell.

30. Forceps according to claim 29, wherein the central portion is raised substantially to the level of the rim, and the base wall of the second half-shell further includes an annular, recessed, peripheral portion.

31. Forceps according to claim 29, wherein the container element is beaker-shaped and is fixed in the hole such that the cavity constitutes a continuation of a space inside the first half-shell.

32. Forceps according to claim 29, wherein the container element includes an open end having a hooked rim for engaging the front rim of the first half-shell.

33. Forceps according to claim 32, wherein the front rim of the first half-shell is a complementary shape of the hooked rim of the container element.

34. Forceps according to claim 29, wherein the container element is beaker-shaped and includes a container base and side walls, and has at least one opening in the container base or in the side walls.

35. Forceps according to claim 29, wherein the hole in the base wall of the first half-shell receives the container element.

36. Forceps for medical use, in particular for biopsy, comprising:
a first and a second half-shell, each having a front rim and a base wall, the first and the second half-shells each being mounted on a support element in a manner such that the first and the second half-shells can adopt a first, open configuration and a second, closed configuration; and
a container element associated with at least the first half-shell, the container element having a cavity for receiving a plurality of biopsy samples, wherein the container element is received in a hole defined by the base wall of the first half-shell,
wherein the second half-shell is not configured to receive a plurality of biopsy samples.

37. Forceps according to claim 36, wherein the base wall of the second half-shell includes a central portion raised substantially to the level of the rim, and an annular, recessed, peripheral portion.

38. Forceps according to claim 36, wherein the container element is beaker-shaped and is fixed in the hole such that the cavity constitutes a continuation of a space inside the first half-shell.

39. Forceps according to claim 36, wherein the container element includes an open end having a hooked rim for engaging the front rim of the first half-shell.

40. Forceps according to claim 39, wherein the engagement of the hooked rim of the open end of the container element with the front rim of the hole of the first half-shell is secured by a mechanical element.

41. Forceps according to claim 40, wherein the mechanical element is a spring ring.

42. Forceps according to claim 39, wherein the front rim of the first half-shell is a complementary shape of the hooked rim of the container element.

43. Forceps according to claim 36, wherein the container element includes a container base and side walls, and has at least one opening in the container base or in the side walls.

44. Forceps according to claim 43, wherein the container element has a plurality of openings in the container base and in the side walls.

45. Forceps according to claim 36, wherein at least a portion of the container element is completely encircled by the base wall.

46. Forceps according to claim 36, wherein the hole is configured to pass the plurality of biopsy samples therethrough.

47. A biopsy forceps, comprising:
a support element;
a first half-shell supported by the support element, the first half-shell having a first front rim and a base wall;
a second half-shell supported by the support element, the second half-shell having a second front rim, the first and the second half-shells being operatively configured to open and close to take biopsy samples; and
a container element affixed to the first half-shell, the container element having a first opening to a cavity for receiving the biopsy samples, and a second opening for discharging fluid from the cavity, wherein the container element is received in a hole defined by the base wall of the first half-shell,
wherein the second half-shell is not configured to receive a plurality of biopsy samples.

48. A biopsy forceps according to claim 47, wherein the second half-shell includes a base wall having a central portion raised substantially to the level of the rim, and an annular, recessed, peripheral portion.

49. A biopsy forceps according to claim 47, wherein the first half-shell includes a hole which communicates with the first opening to the cavity of the container element affixed to the first half-shell.

50. A biopsy forceps according to claim 47, wherein the cavity of the container element is in communication with a space inside the first half shell.

51. Forceps according to claim 47, wherein at least a portion of the container element is completely encircled by the base wall.

52. Forceps according to claim 47, wherein the hole is configured to pass the plurality of biopsy samples therethrough.

53. Forceps for medical use, in particular for biopsy, comprising:
a first and a second half-shell, each having a front rim and a base wall, the first and the second half-shells each being mounted on a support element in a manner such that the first and the second half-shells can adopt a first, open configuration and a second, closed configuration, the first and second half-shells being configured so that the front rims come into contact with each other when in the closed configuration; and
a container element associated with at least the first half-shell, the container element having a cavity for receiving a plurality of biopsy samples,
wherein the second half-shell is not configured to receive a plurality of biopsy samples,
wherein the base wall of the first half-shell includes a hole in which the container element is received.

54. Forceps according to claim 53, wherein the container element includes a container base and side walls, and has at least one opening in the container base or in the side walls.

55. Forceps according to claim 54, wherein the container element has a plurality of openings in the container base and in the side walls.

56. Forceps according to claim 53, wherein the hole communicates with the cavity of the container element associated with the first half-shell.

57. Forceps according to claim 53, wherein the container element is fixed in the hole such that the cavity constitutes a continuation of a space inside the first half-shell.

58. Forceps according to claim 53, wherein the base wall of the second half-shell includes a central portion raised substantially to the level of the rim, and an annular, recessed, peripheral portion.

59. Forceps according to claim 53, wherein at least a portion of the container element is completely encircled by the base wall.

60. Forceps according to claim 53, wherein the hole is configured to pass the plurality of biopsy samples therethrough.

61. Forceps for medical use, in particular for biopsy, comprising:
a first and a second half-shell, each having a front rim and a base wall, the first and the second half-shells each being mounted on a support element in a manner such that the first and the second half-shells can adopt a first, open configuration and a second, closed configuration, wherein the first half-shell includes a hole in the base wall configured to pass a biopsy sample; and
a container element associated with the first half-shell, the container element having an open end for receiving the biopsy sample into a cavity sized to contain a plurality of biopsy samples, the open end corresponding in size to the hole in the base wall of the first half-shell,
wherein the second half-shell is not configured to receive a plurality of biopsy samples.

62. Forceps according to claim 61, wherein the base wall of the second half-shell includes a central portion raised substantially to the level of the rim, and an annular, recessed, peripheral portion.

63. Forceps according to claim 61, wherein the container element is fixed in the hole such that the cavity constitutes a continuation of a space inside the first half-shell.

64. Forceps according to claim 61, wherein the container element includes an open end having a hooked rim for engaging the front rim of the first half-shell.

65. Forceps according to claim 64, wherein the front rim of the first half-shell is a complementary shape of the hooked rim of the container element.

66. Forceps according to claim 61, wherein the container element includes a container base and side walls, and has at least one opening in the container base or in the side walls.

67. Forceps according to claim 61, wherein the hole in the base wall of the first half-shell receives the container element.

* * * * *